US012674197B2

(12) United States Patent (10) Patent No.: US 12,674,197 B2
Davies et al. (45) Date of Patent: Jul. 7, 2026

(54) PROCESS FOR PRODUCING A CHROMATIN CONFORMATION CAPTURE (3C) LIBRARY

(71) Applicant: Oxford University Innovation Limited, Oxford (GB)

(72) Inventors: James Davies, Oxford (GB); James R. Hughes, Oxford (GB)

(73) Assignee: OXFORD UNIVERSITY INNOVATION LIMITED (GB)

( * ) Notice: Subject to any disclaimer, the term of this patent is extended or adjusted under 35 U.S.C. 154(b) by 1047 days.

(21) Appl. No.: 17/426,136

(22) PCT Filed: Feb. 5, 2020

(86) PCT No.: PCT/GB2020/050253
§ 371 (c)(1),
(2) Date: Jul. 28, 2021

(87) PCT Pub. No.: WO2020/161485
PCT Pub. Date: Aug. 13, 2020

(65) Prior Publication Data
US 2022/0098656 A1    Mar. 31, 2022

(30) Foreign Application Priority Data

Feb. 5, 2019    (GB) ..................................... 1901576

(51) Int. Cl.
*C12Q 1/6858*    (2018.01)
*C12Q 1/6806*    (2018.01)
(52) U.S. Cl.
CPC ......... *C12Q 1/6858* (2013.01); *C12Q 1/6806* (2013.01)
(58) Field of Classification Search
CPC ................ C12Q 1/6858; C12Q 1/6806; C12Q 2521/301; C12Q 2535/122
See application file for complete search history.

(56) References Cited

U.S. PATENT DOCUMENTS

| | | | |
|---|---|---|---|
| 5,731,153 A | 3/1998 | Lucas et al. | |
| 2003/0170689 A1 | 9/2003 | Stamatoyannapoulos et al. | |
| 2007/0141584 A1 | 6/2007 | Roberts et al. | |
| 2009/0215029 A1 | 8/2009 | Lawler et al. | |
| 2010/0081141 A1 | 4/2010 | Chen et al. | |
| 2013/0096009 A1 | 4/2013 | Dekker et al. | |
| 2013/0183672 A1 | 7/2013 | de Laat et al. | |
| 2015/0123588 A1 | 5/2015 | Yoshida et al. | |
| 2017/0362649 A1 | 12/2017 | Lieberman-Aiden et al. | |

FOREIGN PATENT DOCUMENTS

| | | |
|---|---|---|
| EP | 2 591 125 A2 | 5/2013 |
| EP | 2 986 761 B1 | 2/2016 |
| EP | 3 334 841 A1 | 6/2018 |
| EP | 3 360 975 A1 | 8/2018 |
| EP | 3 366 818 A1 | 8/2018 |

| | | |
|---|---|---|
| EP | 3688157 A1 | 8/2020 |
| EP | 3 754 027 A1 | 12/2020 |
| GB | 2517936 A | 11/2015 |
| WO | 2009/099602 A1 | 8/2009 |
| WO | 2012/061600 A1 | 5/2012 |
| WO | 2012/108864 A1 | 8/2012 |
| WO | 2012/159025 A2 | 11/2012 |
| WO | 2014/168575 A1 | 10/2014 |
| WO | 2014205296 A1 | 12/2014 |
| WO | 2015/033134 A1 | 3/2015 |
| WO | 2015071748 A1 | 5/2015 |
| WO | 2016019360 A1 | 2/2016 |
| WO | 2016/089920 A1 | 6/2016 |
| WO | 2017034970 A1 | 3/2017 |
| WO | 2017/068379 A1 | 4/2017 |
| WO | 2017176971 A1 | 10/2017 |
| WO | 2018045137 A1 | 3/2018 |
| WO | 2018045141 A1 | 3/2018 |
| WO | 2018/232396 A1 | 12/2018 |
| WO | 2019/023214 A1 | 1/2019 |
| WO | 2019060907 A1 | 3/2019 |
| WO | 2019076768 A1 | 4/2019 |

OTHER PUBLICATIONS

Hsieh et al. (Mapping Nucleosome Resolution Chromosome Folding in Yeast by Micro-C. Cell (2015), 162(1): 108-119. (Year: 2015).*
Nagano et al. (Comparison of Hi-C results using in-solution versus in nucleus ligation. Genome Biology (2015), 16: 175-, p. 1-13) (Year: 2015).*
International Search Report and Written Opinion for WO 2020/161485 (PCT/GB2020/050253), dated May 13, 2020, pp. 1-15.
UK Search Report for GB 1901576.7, dated Sep. 12, 2019, pp. 1-5.
Takashi Nagano et al: "Comparison of Hi-C results using in-solution versus in-nucleus ligation", Genome Biology, vol. 16, No. 1, Aug. 26, 2015 (Aug. 26, 2015), XP055584818, DOI:-10.1186/s13059-015-0753-7, pp. 9-10.
Tsu Ng-Han S. Hsi Eh et al: "Mapping Nucleosome Resolution Chromosome Folding in Yeast by Micro-C", Cell, vol. 162, No. 1, Jul. 1, 2015 (Jul. 1, 2015), pp. 108-119, XP055616476, Amsterdam, NL ISSN: 0092-8674, DOI: 10.1016/j.cell.2015.05.048, p. 10.
Anthony D. Schmitt et al: "Genome-wide mapping and analysis of chromosome architecture", Nat Rev Mol Cell Biol., vol. 17, No. 12, Sep. 1, 2016 (Sep. 1, 2016), pp. 743-755, XP055616481, London.
Ohno et al "Sub-nucleosomal Genome Structure Reveals Distinct Nucleosome Folding Motifs," Cell (2019), https://doi.org/10.1016/j.cell.2018.12.014.

(Continued)

*Primary Examiner* — Iqbal H Chowdhury
(74) *Attorney, Agent, or Firm* — MORRISON & FOERSTER LLP

(57) ABSTRACT

The present invention relates to a process for producing a chromatin conformation capture (3C) library. This may be used for identifying nucleic acid regions within a nucleic acid sample which interact with one another. The process comprises treating nucleic acids in a population of eukaryotic cells, the process comprising the steps: (i) immobilising the nucleic acids within the cells in a population of eukaryotic cells; (ii) permeabilising or removing the cell membranes of the eukaryotic cells; and (iii) fragmenting the immobilised nucleic acids within the cells to produce nucleic acid fragments.

12 Claims, 8 Drawing Sheets

(56)                  References Cited

OTHER PUBLICATIONS

Wang, Z., Gerstein, M. & Snyder, M RNA-Seq: a revolutionary tool for transcriptomics. Nat Rev Genet 10, 57-63 (2009).

Mikkelsen, T.S. et al Genome-wide maps of chromatin state in pluripotent and lineage-committed cells. Nature 448, 553-60 (2007).

Robertson, G. et al. Genome-wide profiles of STAT1 DNA association using chromatin immunoprecipitation and massively parallel sequencing. Nat Methods 4, 651-7 (2007).

Hesselberth, J.R. et al Global mapping of protein-DNA interactions in vivo by digital genomic footprinting. Nat Methods 6, 283-9 (2009).

Tolhuis, B., Palstra, R.J., Splinter, E., Grosveld, F. & de Laat, W. Looping and interaction between hypersensitive sites in the active beta-globin locus. Mol Cell 10, 1453-65 (2002).

Sanyal, A., Lajoie, B.R., Jain, G. & Dekker, J. The long-range interaction landscape of gene promoters. Nature 489, 109-13 (2012).

De Laat, W. & Duboule, D. Topology of mammalian developmental enhancers and their regulatory landscapes. Nature 502, 499-506 (2013).

Davies J.O.J., Telenius J.M., McGowan S., Roberts N.A., Taylor S., Higgs D.R. and Hughes J.R. 'Multiplexed analysis of chromosome conformation at vastly improved sensitivity', Nature Methods 2016; 13, 74-80.

Hughes et al. Analysis of hundreds of cis-regulatory landscapes at high resolution in a single, high-throughput experiment. Nat Genet (2014) + supplementary.

Pasquali et al. Pancreatic islet enhancer clusters enriched in type 2 diabetes risk-associated variants. Nat Genet 46, 136-43 (2014).

Maurano et al. Systematic localization of common disease-associated variation in regulatory DNA. Science 337, 1190-5 (2012).

Parker et al. Chromatin stretch enhancer states drive cell-specific gene regulation and harbor human disease risk variants. Proc Natl Acad Sci U S A 110, 17921-6 (2013).

Rao et al. A 3D map of the human genome at kilobase resolution reveals principles of chromatin looping. Cell 159, 1665-80 (2014).

Jager, R. et al. Capture Hi-C identifies the chromatin interactome of colorectal cancer risk loci. Nat Commun 6, 6178 (2015).

Schoenfelder et al. The pluripotent regulatory circuitry connecting promoters to their long-range interacting elements. Genome Res 25, 582-97 (2015).

Vernimmen et al. Long-range chromosomal interactions regulate the timing of the transition between poised and active gene expression. EMBO J 26, 2041-51 (2007).

Hughes, J.R. et al. High-resolution analysis of cis-acting regulatory networks at the alpha-globin locus. Philos Trans R Soc Lond B Biol Sci 368, 20120361 (2013).

Bau et al. The three-dimensional folding of the alpha-globin gene domain reveals formation of chromatin globules. Nat Struct Mol Biol 18, 107-14 (2011).

Simonis et al. Nuclear organization of active and inactive chromatin domains uncovered by chromosome conformation capture-on-chip (4C). Nat Genet 38, 1348-54 (2006).

Kang et al. Genomic organization, tissue distribution and deletion mutation of human pyridoxine 5'-phosphate oxidase. Eur J Biochem 271, 2452-61 (2004).

Love et al. Moderated estimation of fold change and dispersion for RNA-seq data with DESeq2. Genome Biol 15, 550 (2014).

Klein et al. FourCSeq: analysis of 4C sequencing data. Bioinformatics (2015).

Thongjuea et al. r3Cseq: an R/Bioconductor package for the discovery of long-range genomic interactions from chromosome conformation capture and next-generation sequencing data. Nucleic Acids Res 41, e132 (2013).

Osborne et al. Active genes dynamically colocalize to shared sites of ongoing transcription. Nat Genet 36, 1065-71 (2004).

Noordermeer et al. Variegated gene expression caused by cell-specific long-range DNA interactions. Nat Cell Biol 13, 944-51 (2011).

Bernet et al. Targeted inactivation of the major positive regulatory element (HS-40) of the human alpha-globin gene locus. Blood 86, 1202-11 (1995).

Anguita et al. Deletion of the mouse alpha-globin regulatory element (HS-26) has an unexpectedly mild phenotype. Blood 100, 3450-6 (2002).

De Wit and de Laat. A decade of 3C technologies: insights into nuclear organization. Genes Dev 26, 11-24 (2012).

Takahashi and Yamanaka. Induction of pluripotent stem cells from mouse embryonic and adult fibroblast cultures by defined factors. Cell 126, 663-76 (2006).

Kowalczyk, M.S. et al. Intragenic enhancers act as alternative promoters. Mol Cell 45, 447-58 (2012).

Magoc and Salzberg. FLASH: fast length adjustment of short reads to improve genome assemblies. Bioinformatics 27, 2957-63 (2011).

Kent et al. The human genome browser at UCSC. Genome Res 12, 996-1006 (2002).

Raney et al. Track data hubs enable visualization of user-defined genome-wide annotations on the UCSC Genome Browser. Bioinformatics 30, 1003-5 (2014).

Office Action for Japanese Patent Application 2021-545989, dated Jan. 30, 2024, pp. 1-10 (English translation included).

Extended European Search Report for Patent Application 23205611. 9, dated Feb. 16, 2024, pp. 1-10.

Zhongliang Zhao et al., "Nucleosome Positioning Assay", bio-protocol, vol. 7, Iss 10, May 20, 2017 DOI:10.21769/BioProtoc. 2285, pp. 1-9 (Copyright © 2017 the Authors; exclusive licensee Bio-protocol LLC. 1).

Brian Spetman et al., "Microarray Mapping of Nucleosome Position", 2011, pp. 1-15.

James O J Davies et al., "Multiplexed analysis of chromosome conformation at vastly improved sensitivity", Nature Methods, Nov. 23, 2015, vol. 13, No. 1, p. 74-80, DOI: 10.1038/nmeth. 3364.

Nils Krietenstein et al., "Ultrastructural Details of Mammalian Chromosome Architecture", Krietenstein et al., 2020, Molecular Cell 78, 554-565 May 7, 2020 © 2020 Elsevier Inc., pp. 1-20.

Sati and Cavalli, "Chromosome conformation capture technologies and their impact in understanding genome function", 2017, Chromosoma (2017) 126:33-44.

International Preliminary Report on Patentability received for PCT Patent Application No. PCT/GB2020/050253, mailed on Aug. 19, 2021, 8 pages.

Kakui, Y. et al. (Oct. 2017, e-pub. Aug. 21, 2017). "Condensin-Mediated Remodeling of the Mitotic Chromatin Landscape in Fission Yeast", Nature Genetics 49(10):1553-1557, 11 pages.

Peng, H. et al. (Jul. 1, 2021, e-pub Jun. 9, 2021). "Defining Genome Architecture at Base-Pair Resolution", Nature 595(7865):125-129.

Office Action for United Kingdom Patent Application GB1901576. 7, dated Nov. 11, 2022, pp. 1-5.

Skene & Henikoff, "A simple method for generating high-resolution maps of genome-wide protein binding", article No. e09225 eLife, vol. 4, 2015.

Ferrai et al, "A Transcription-dependent Micrococcal Nuclease-resistant Fragment of the Urokinase-type Plasminogen Activator Promoter Interacts with the Enhancer," pp. 12537-12546 Journal of Biological Chemistry, vol. 282, No. 17, 2007.

Skene et al, "Targeted in situ genome-wide profiling with high efficiency for low cell numbers", pp. 10061019. Nature Protocols, vol. 13, No. 5, 2018.

Jörg Langowski (2010) Chromosome conformation by crosslinking, Nucleus, 1:1, 37-39.

Erez Lieberman-Aiden et al. Comprehensive Mapping of Long-Range Interactions Reveals Folding Principles of the Human Genome Oct. 9, 2009, Science 326, 289 (2009)& Supporting Online Material.

International Search Report and Written Opinion for WO 2017/ 068379 (PCT/GB2016/053314), dated Jan. 26, 2017, pp. 1-10.

International Preliminary Report on Patentability for WO 2017/ 068379 (PCT/GB2016/053314), dated Apr. 24, 2018, pp. 1-14.

UK Search Report for GB 1518843.6, dated Sep. 14, 2016, pp. 1-33.

Prediger "Understanding how distal regulatory elements control gene expression. Next generation chromosomal conformational capture (NG Capture-C) Technology." Decoded. 1-8. 2015.

(56)     References Cited

OTHER PUBLICATIONS

Ay et al, Identifying multi-locus chromatin contacts in human cells using tethered multiple 3C, BMC Genomics, 16 (1), 2015.

Selvaraj et al, whole-genome haplotype reconstruction using proximity-litigation and shotgun sequencing, Nature Biotechnology, 31(12), 2013.

Zhang et al, ChIA-PET analysis of transcriptional chromatin interactions, Methods, 58(3), 2012.

Duan et al, A genome-wide 3C-method for characterising the three-dimensional architectures of genomes, Methods, 58(3), 2012.

Kolovos et al Targeted chromatin capture (T2C): a novel high resolution high throughput method to detect genomic interactions and regulatory elements. Epigenetics & Chromatin. 7(1). 2014. p. 10.

Hughes Abstract from Annual Conference on Hemoglobin switching, Jun. 7-11, 2012.

Hughes et al Abstract for EMBO Nuclear Structure and Dynamics meeting Oct. 2-6, 2013 "Linking promoters with their regulatory elements during erythropoiesis".

Davies Powerpoint presentation: "Linking promoters with their regulatory elements during erythropoiesis" presented at EMBO Nuclear Structure and Dynamics meeting Oct. 2-6, 2013.

Davies Poster "Next Generation Capture C: a highly sensitive and scalable method for multiplexed definition of chromatin structure", presented in entrance hall of SAID Business School Mar. 27, 2015.

Davies Powerpoint presentation "Next Generation Capture C: a highly sensitive and scalable method for multiplexed definition of chromatin structure", presented Jul. 9, 2015 to internal meeting of Oxford Medical Sciences Division.

Sexton et al Nature Protocols, vol. 7 issue 7, 2012, 'Sensitive detection of chromatin coassociations using enhanced chromosome conformation capture on chip' pp. 1335-1350.

Davies J.O.J., Oudelaar A.M., Higgs D.R. and Hughes J.R How best to identify chromosomal interactions: a comparison of approaches. Nature Methods 2017, 14 (2), 125-134.

Hsieh T.S. Fudenberg G., Goloborodko A., Rando O.J. Micro-C XL: assaying chromosome conformation from the nucleosome to the entire genome. Nat Methods. Dec. 2016;13(12):1009-1011.

Buenrostro, J.D., Giresi, P.G., Zaba, L.C., Chang, H.Y. & Greenleaf, W.J., "Transposition of native chromatin for fast and sensitive epigenomic profiling of open chromatin, DNA-binding proteins and nucleosome position", Nat Methods 10, 1213-8 (2013).

Buenrostro et al. "Transposition of native chromatin for multimodal regulatory analysis and personal epigenetics" Nat Methods, 2013, 10(12) 1213-1218.

Noordermeer, D. et al., "The dynamic architecture of Hox gene clusters", Science 334, 222-5 (2011).

Van de Werken, H.J. et al., "Robust 4C-seq data analysis to screen for regulatory DNA interactions", Nat Methods 9, 969-72 (2012).

Dekker, J., Rippe, K., Dekker, M. & Kleckner, N., "Capturing chromosome conformation", Science 295, 1306-11 (2002).

Kornberg, R.D. et al. (1989). "Preparation of Nucleosomes and Chromatin," Methods Enzymol. 170:3-14.

Widlak, P. et al. (Jun. 14, 2002). "Modeling Apoptotic Chromatin Condensation in Normal Cell Nuclei," The Journal of Biological Chemistry 277(24):21683-21690.

* cited by examiner

Alpha globin locus 100 kb

Alpha globin locus 1 kb

Chromosome 9, 280,001-280,000

Chromosome 10, 230,001-280,000

PROCESS FOR PRODUCING A CHROMATIN CONFORMATION CAPTURE (3C) LIBRARY

CROSS-REFERENCE TO RELATED APPLICATIONS

This application is the National Stage of International Application No. PCT/GB2020/050253, filed Feb. 5, 2020, which claims priority to GB 1901576.7, filed Feb. 5, 2019, which are entirely incorporated herein by reference.

The present invention relates to a process for producing a chromatin conformation capture (3C) library. This may be used for identifying nucleic acid regions within a nucleic acid sample which interact with one another.

Progress in our ability to annotate regulatory elements in the genome and determine their potential function has been driven by technological advances, such as RNA-seq [1], ChIP-seq [2-3], DNase-seq [4] and ATAC-seq [5]. However, an outstanding challenge is to understand the mechanisms by which regulatory elements control specific gene promoters at a distance (10s to 1000s kb).

Using conventional Chromosome Conformation Capture (3C), it is possible to analyse in detail the interactions between enhancers, silencers, boundary elements and promoters at individual loci at high resolution [6-11].

Since the development of the original 3C method in 2002 [6], several new 3C-based techniques have emerged such as Capture-C, Hi-C, Capture Hi-C, in situ Hi-C, Circularized Chromosome Conformation Capture (4C), 4C-seq, ChIA-PET, Carbon Copy Chromosome Conformation Capture (5C) and NG Capture-C [12,13] (WO2017/068379). Each of these techniques has its particular strengths and weaknesses.

There is still a need for more chromosome conformation capture protocols with increased sensitivity and resolution, that are straightforward to perform, but which can generate data in a high-throughput manner.

The resolution of these methods remains limited when studying mammalian genomes. In most assays, the resolution is determined by the bin size used to pool data and improve signal strength. This is a function of the depth of sequencing and the size of the organism's genome (the sequencing requirements increase with the square of the genome size or resolution). If sufficient sequence depth can be obtained then the limiting factor becomes the restriction fragment size, which equates to a theoretical limit of ~256 bp with 4 cutter restriction enzymes (which are the highest resolution enzymes generally used in 3C library preparation at present). Although non-sequence dependent nucleases such as DNaseI and Micrococcal nuclease have previously been used to generate 3C libraries, the enrichment steps used in these previous protocols have not resulted in data with higher resolution than restriction enzymes in larger mammalian genomes [14,15].

Increases in resolution are potentially useful for highlighting the regulatory sequences that control genes in greater detail and to identify novel sequences that control genes. Increases in resolution should also allow single nucleotide polymorphisms identified by genome wide association studies to be linked to the genes or other aspects of genome function or structure that they control with greater confidence. This has potential benefits for personalised medicine, diagnostics and drug discovery.

The best resolution which was previously obtainable was with next generation Capture-C [12,13].

The inventors have now found that a significant improvement in resolution may be obtained using the process of the invention. Using this process, single-base pair resolutions may be obtained; this resolution is over an order of magnitude greater than that obtainable by previous methods.

The process of the invention involves a novel combination of fixation and digestion steps in the production of the 3C library.

In previous methods (e.g. WO2017/068379), the cells have been fixed (e.g. using formaldehyde) and then homogenised in order to break open the cells and to release the chromatin. In the process of the current invention, the cells are fixed but are then permeabilised (to allow digestion). It has been found that this gentler method contributes to a greater resolution.

Digestion of the chromatin has previously been carried out using a number of different enzymes, including 4 and 6 base-pair cutting restriction endonucleases, e.g. HindIII, EcoRI, NcoI, XbaI, BglIII, DpnII and NlaIII, and bacterial nucleases including Micrococcal nuclease and DNaseI.

The inventors have now found that micrococcal nuclease, when used in the process of the invention, contributes to the enhanced resolution obtained.

Although micrococcal nuclease has been previously used to map nucleosome resolution chromosome folding in yeast [14,15], the resolutions previously obtained were stated to be between 200 bp and ~4 kb. Furthermore, whilst yeast (*S. cereviseae*) cells are eukaryotic cells, the *S. cerevisiae* genome is about 12 million base pairs, which is only about 1/250th the size of the human genome.

The process of the invention therefore allows the interactions of regulatory elements in mammalian genes, inter alia, to be studied at a previously-unobtainable resolution.

In one embodiment, the invention provides a process for treating nucleic acids in a population of eukaryotic cells, the process comprising the steps:

(i) immobilising the nucleic acids within the cells in a population of eukaryotic (preferably mammalian) cells;

(ii) permeabilising or removing the cell membranes of the eukaryotic (preferably mammalian) cells; and (iii) fragmenting the immobilised nucleic acids within the cells to produce nucleic acid fragments.

Preferably, the cells are mammalian cells.

In a preferred embodiment, the invention provides a process for treating nucleic acids in a population of eukaryotic (preferably mammalian) cells, the process comprising the steps:

(i) cross-linking the nucleic acids within the cells in a population of eukaryotic (preferably mammalian) cells;

(ii) permeabilising or removing the cell membranes of the eukaryotic (preferably mammalian) cells; and (iii) fragmenting the cross-linked nucleic acids within the cells to produce nucleic acid fragments.

Preferably, the nucleic acids are chromatin.

In another embodiment, the invention provides a process for producing a 3C library, the process comprising the steps:

(a) treating nucleic acids by a process of the invention for treating nucleic acids in a population of eukaryotic cells;

(b) ligating the nucleic acid fragments to produce ligated nucleic acid fragments; and (c) de-immobilising (e.g. de-crosslinking) the ligated nucleic acid fragments.

In another embodiment, the invention provides a method of identifying nucleic acid regions within a nucleic acid sample which interact with one another, the method comprising the steps:

producing a 3C library by a process for producing a 3C library of the invention;

(d) fragmenting the 3C library to produce nucleic acid fragments;

(e) optionally, adding sequencing adaptors to the ends of the nucleic acid fragments and/or amplifying the nucleic acid fragments;

(f) contacting the nucleic acid fragments with a targeting nucleic acid which binds to a subgroup of the nucleic acid fragments, wherein the targeting nucleic acid is labelled with the first half of a binding pair;

(g) isolating the subgroup of nucleic acid fragments which have been bound by the targeting nucleic acid using the second half of the binding pair;

(h) amplifying the isolated subgroup of nucleic acid fragments;

(j) optionally repeating Steps (f), (g) and (h) one or more times; and (k) optionally sequencing the amplified isolated subgroup of nucleic acid fragments.

Preferably, the targeting nucleic acid is a DNA oligonucleotide. Preferably, the nucleic acid sample is a sample of eukaryotic cells, preferably mammalian cells.

In a further embodiment, there is provided a method of identifying allele-specific interaction profiles in SNP-containing regions of nucleic acids, the method comprising a method of the invention including sequencing the amplified isolated subgroup of nucleic acid fragments in order to identify allele-specific interaction profiles in SNP-containing regions.

In a yet further embodiment, there is provided a kit for identifying nucleic acid regions within a nucleic acid sample which interact with one another, the kit comprising buffers and reagents for performing a method of the invention.

In a yet further embodiment, there is provided a method of identifying one or more interacting nucleic acid regions that are indicative of a particular disease state or disorder, the method comprising:

a) carrying out a method as defined herein on a nucleic acid sample of eukaryotic (preferably mammalian) cells obtained from a subject with a particular disease state or disorder;

b) quantifying a frequency of interaction between a first nucleic acid region and a second nucleic acid region; and c) comparing the frequency of interaction in the nucleic acid sample from the subject with said disease state or disorder with the frequency of interaction in a control nucleic acid sample from a healthy subject, such that a difference in the frequency of interaction in the nucleic acid samples is indicative of a particular disease state or disorder.

The process of the invention relates to the treating of the nucleic acids within a population of eukaryotic cells. The nucleic acids are treated in situ, i.e. within the cells.

The nucleic acid sample may comprise a population of eukaryotic cells.

Examples of eukaryotic cells include cells from animals, plants and fungi. Preferably, the eukaryotic cells are higher eukaryote cells or cells from multicellular organisms. The plants may be monocots or dicots. In some embodiments, the eukaryotic cells are animal cells, preferably vertebrate cells, and more preferably mammalian cells.

Preferably, the mammalian cells are from a human, monkey, mouse, rat, rabbit, guinea pig, sheep, horse, pig, cow, goat, dog or a cat. Most preferably, the mammalian cells are human cells.

In some embodiments, the cells are erythroid cells or stem cells (e.g. embryonic stem cells). Preferably, the nucleic acids are obtained from live cells.

In some preferred embodiments, the population of cells consists of $10^4$ to $10^9$ cells, more preferably $10^6$ to $10^8$ cells. In other preferred embodiments, the population of cells consists of 1-10,000 cells, 10,000-1 million cells, or 1 million to 100 million cells.

As used herein, the term "nucleic acid" encompasses chromatin, DNA and RNA. Preferably, the nucleic acid is DNA or chromatin, most preferably chromatin. Chromatin comprises nucleosomes which are linked by inter-nucleosomal linkers.

Step (i) comprises immobilising (e.g. cross-linking) the nucleic acids within the cells in a population of eukaryotic (preferably mammalian) cells. The immobilisation (e.g. cross-linking) is carried out on an individual-cell basis (i.e. immobilisation, e.g. crosslinking, within a cell). The immobilisation (e.g. cross-linking) is carried out in situ, i.e. within the cell nucleus. Preferably, the immobilisation (e.g. cross-linking) is carried out within substantially all or all of the cells in the population of eukaryotic (preferably mammalian) cells.

In this step, the nucleic acids (e.g. within chromatin) are immobilised (e.g. cross-linked) such that regions within the nucleic acids which were interacting with one another are held or fixed in close proximity.

The nucleic acid regions which interact with one another are particularly DNA elements which affect or control the expression of an associated gene or other aspects of genome function or structure. For example, the DNA elements may be promoters, enhancers, insulators and/or silencers.

The nucleic acids may be immobilised by cross-linking the nucleic acids or by embedding the nucleic acids in an immobilising agent, inter alia.

The regions of nucleic acids which were interacting with one another may be cross-linked directly (i.e. nucleic acid to nucleic acid) or indirectly (e.g. by cross-linking of the nucleic acids to moieties (e.g. proteins) which are bound to the nucleic acids or between proteins bound to nucleic acid directly or indirectly). Preferably, the nucleic acids are cross-linked using a cross-linking reagent. The cross-linking agent must be one which is capable of entering into (unpermeabilised) cells. Preferably, the cross-linking agent is formaldehyde.

The immobilising agent is a substance which is capable of entering into (un-permeabilised) cells and of immobilising the nucleic acids within those cells such that regions within the nucleic acids which were interacting with one another are held or fixed in close proximity. In some embodiments, the eukaryotic (preferably mammalian) cells are immobilised within plugs of the immobilising agent. Examples of immobilising agents include gels, preferably hydrogels, formed from cross-linked polymers.

A hydrogel is a network of polymer chains that are hydrophilic, sometimes found as a colloidal gel, in which water is the dispersion medium. The structure of the hydrogel may be changed by varying the concentration of the hydrogel-forming polymer in the hydrogel. Examples of hydrogel polymers include polyvinyl alcohol, acrylate polymers (e.g. sodium acrylate) and polymers with an abundance of hydrophilic groups. Other hydrogel polymers include agarose, alginate, methylcellulose, hyaluronan, Elastin-like polypeptides and other naturally-derived polymers. Preferably, the immobilising agent is agarose gel.

Step (ii) comprises permeabilising or removing the cell membranes of the eukaryotic (preferably mammalian) cells. In this step, the outer cell membrane and the nuclear membrane of the cells are at least permeabilised in order to allow the fragmenting enzyme(s) to gain access to the nucleic acids in the nucleus (e.g. to the chromatin).

As used herein, the term "permeabilise" means that the outer cell membrane and nuclear membranes are rendered permeable to fragmenting enzyme(s), but the membranes remain otherwise intact.

In some embodiments, the outer cell membrane and/or nuclear membrane is not lysed.

In some embodiments, the outer cell membrane and/or nuclear membrane is not partially or completely destroyed. In some embodiments, the outer cell membrane and/or nuclear membrane is not partially or completely removed.

In one preferred embodiment, the outer cell membranes and nuclear membranes of the eukaryotic (preferably mammalian) cells are permeabilised without removing the outer cell membranes or nuclear membranes. In other embodiments, the cell membrane is removed and the nuclear membrane is permeabilised (but not removed). The chromatin, enclosed by a permeabilised nuclear membrane, may then be isolated. In other embodiments, the cell membrane is removed and the nuclear membrane is removed. The chromatin may then be isolated.

In embodiments wherein the cell membranes of the cells are permeabilised or removed, they are preferably permeabilised or removed in substantially all or all of the cells, respectively. In embodiments wherein the nuclear membranes of the cells are permeabilised or removed, they are preferably permeabilised or removed in substantially all or all of the cells, respectively.

The outer cell membrane and the nuclear membrane are permeabilised using a membrane-permeabilising agent. Examples of membrane-permeabilising agents include Digitonin, Saponin, Tergitol-type NP40, Triton X-100, Sodium dodecyl sulphate and Tween 20. Preferably, the permeabilising agent is digitonin (e.g. from Sigma).

In one embodiment. the amount of permeabilising agent used is that which is enough to permeabilise the outer cell membranes and nuclear membranes of the cells, preferably without partially or completely removing the cell membrane and/or nuclear membrane. Higher amounts of permeabilising agent may be used to completely remove the outer cell membranes and nuclear membranes of the cells. Intermediate amounts of permeabilising agent may be used to completely remove the outer cell membranes and to permeabilise the nuclear membranes of the cells.

Step (iii) comprises fragmenting the immobilised (e.g. cross-linked) nucleic acids (e.g. chromatin) within the cells to produce nucleic acid fragments. The nucleic acid fragments are preferably chromatin or DNA fragments.

In this step, the immobilised (e.g. cross-linked) nucleic acids (e.g. chromatin) are fragmented in order to allow them subsequently to be ligated to other nucleic acid sequences within chromatin that were in close physical proximity in the nucleus at the time of fixation. In this fragmentation step, the inter-nucleosome linkers are cleaved and their lengths are preferably reduced.

Following fragmentation, the free ends of nucleic acid within chromatin are joined to one another using a ligation reaction. This produces a 3C library in which the order of the nucleic acid fragments are rearranged to reflect their proximity in 3 dimensional space at the time of immobilisation/fixation rather than their original position in the linear nucleic acid molecule.

The fragmenting step should preferably not affect the integrity of the immobilisation (e.g. cross-linking) or not substantially affect the integrity of the immobilisation (e.g. cross-linking).

The fragmenting may be carried out by any suitable manner. Examples of fragmenting processes include using an enzyme, e.g. an endonuclease. In some embodiments, the fragmenting is carried out using restriction endonucleases, most preferably using restriction endonucleases which recognise 4 base pairs (e.g. DpnII or NlaIII).

In some embodiments of the invention, the fragmentation step does not comprise the step of labelling the free ends of the nucleic acid fragments with the first half of a binding pair. In particular, in some embodiments of the invention, the fragmentation step does not comprise the step of labelling the free ends of the nucleic acid fragments with biotin.

In a particularly-preferred embodiment of the invention, the fragmenting is carried out using an endo-exonuclease. Preferably, the endo-exonuclease is micrococcal nuclease (EC 3.1.31.1). Micrococcal nuclease preferentially digests single-stranded nucleic acids. The enzyme is also active against double-stranded DNA and RNA and all sequences will be ultimately cleaved.

The fragmenting of the immobilised (e.g. cross-linked) nucleic acids (e.g. chromatin) is not carried out to completion. In particular, the inter-nucleosomal linkers are not all cut/digested in the fragmenting step. Preferably, the fragmenting of the immobilised (e.g. cross-linked) nucleic acids (e.g. immobilised or cross-linked chromatin) is carried out such that all or substantially all of the inter-nucleosomal linkers are kept intact. Preferably, the chromatin is digested to produce >70% (preferably >80% or >90%) mono-nucleosomes.

The inter-nucleosomal linkers are preferably kept at least partially intact (i.e. not digested to completion), but may be cleaved. Preferably, the inter-nucleosomal linkers are of the length 10-500, 10-200, 50-200 or 10-100 base pairs after fragmentation (e.g. digestion).

Preferably, the nucleic acid (e.g. chromatin) is fragmented (e.g. digested) to mono-nucleosomes (e.g. 180-200 bp) and more preferably with the inter-nucleosomal linkers attached. Preferably, the nucleic acid which is wrapped around the histone core of the nucleosome is not fragmented (digested).

The duration of the fragmentation step and/or the amount/concentration of the fragmenting enzyme (when used) are selected so as to achieve this.

Preferably, a relatively long incubation time in combination with a very small quantity of enzyme is used. This creates greater control over the reaction compared to shorter incubation times with more enzyme.

The degree of chromatin fragmentation and extent of inter-nucleosomal linker degradation may readily be assayed by gel electrophoresis, e.g. by using an automated system such as the Agilent TapeStation (D1000 reagents).

After the fragmentation step (i.e. Step (iii)), immobilised (e.g. cross-linked) nucleosomes may be linked together using DNA adaptors (e.g. as shown in Ohno et al., Sub-nucleosomal Genome Structure Reveals Distinct Nucleosome Folding Motifs, Cell (2019), doi.org/10.1016/j.cell.2018.12.014). For example, the DNA adaptors may be ligated to the DNA entry end and DNA exit end of the DNA molecules in the nucleosomes. The adaptors might be labelled (e.g. biotin-conjugated). In other embodiments, the adaptors are not labelled (e.g. they are not biotin-conjugated).

In other embodiments of the invention, there is provided a process for producing a 3C library, the process comprising the steps:

(a) treating nucleic acids by a process of the invention for treating nucleic acids in a population of eukaryotic (preferably mammalian) cells;

(b) ligating the nucleic acid fragments to produce ligated nucleic acid fragments; and (c) de-immobilising (e.g. de-crosslinking) the ligated nucleic acid fragments.

As used herein, the term "3C library" refers to a library of DNA fragments, wherein the DNA fragments comprise contiguously-joined DNA elements wherein the DNA elements are ones which are capable of interacting with one another (for example within a cell).

Step (b) comprises ligating the nucleic fragments obtained from Step (a) to produce ligated nucleic acid fragments. The ligated nucleic acid fragments are preferably ligated chromatin fragments or ligated DNA fragments.

In this step, the free ends of the nucleic acid fragments which were produced in Step (iii) are ligated together in order to produce ligated nucleic acid fragments.

Ligation will occur in a random manner between the free ends of the nucleic acid fragments. However, ligation will occur most preferably between adjacent free nucleic acid ends which are held in close proximity to one another by the immobilisation (e.g. cross-linking) process of Step (i). In this way, regions of nucleic acid within the nucleic acid sample which previously interacted with one another will now preferably become chemically joined (ligated) to one another.

Preferably, the length of the ligated nucleic acid fragments is greater than 200 bp (i.e. there is an increase in fragment size in profile of the DNA fragment lengths, preferably such that there is very little DNA of the size of fragments in the main mono-nucleosomal peak following the digestion reaction (see FIG. 2).

Prior to ligation, the ends of the nucleic acid fragments are preferably blunted and phosphorylated, e.g. using T4 poly-nucleotide kinase (PNK) and DNA Polymerase I, Large (Klenow) Fragment.

Ligation may be carried out using any suitable ligating agent, e.g. a ligase. Preferably, the ligase is a DNA ligase. Examples of suitable DNA ligases include T4 DNA ligase.

In Step (c), the ligated nucleic acid fragments are de-immobilised (e.g. de-crosslinked). If the cells have not already been lysed, then they may lysed at this time.

If the cell membranes have not previously been removed, then the cell membranes are also removed at this time, e.g. with a lysis buffer, proteinase K and heat treatment or suitable detergent. Alternatively, sufficient amounts of a permeabilising agent (e.g. as disclosed herein) may be used. In some preferred embodiments, the nuclear and/or cell membranes are not removed until this step.

In this step, the ligated nucleic acid fragments (e.g. ligated chromatin fragments) are de-immobilised (e.g. decross-linked) in order to produce linear nucleic acid fragments (e.g. linear chromatin fragments). For example, the immo-bilising agent is removed/dissolved or the crosslinking moi-eties are cleaved or removed.

In some embodiments, the crosslinks are removed by heating the ligated nucleic acid fragments to a high tem-perature, such as to 50° C., 60° C., 70° C., 80° C. or greater. The de-crosslinking is preferably carried out using Protei-nase K. Optionally, non-nucleic acid material (e.g. proteins, cross-linking agents, etc.) is also removed at this time. It is also preferable to remove RNA from the sample at this point, preferably using RNase. For example, the ligated nucleic acid fragments may be extracted with phenol/chloroform or solid phase extraction methods (such as Qiagen spin col-umns).

In yet another embodiment, the invention provides a method of identifying nucleic acid regions within a nucleic acid sample which interact with one another.

The first step of this method comprises producing a 3C library by a process of the invention, i.e. Steps (a), (b) and (c) as described above.

In Step (d), the nucleic acid fragments in a 3C library are fragmented. The nucleic acid fragments are preferably DNA fragments. In this step, the lengths of the nucleic acid fragments in the 3C library are preferably reduced to a size which is suitable for high throughput sequencing, capture and/or amplification.

Preferably, the lengths of the nucleic acid fragments are reduced to 100-500 base pairs, more preferably 100-300 or 150-250 base pairs, and most preferably to about 250 base pairs.

Fragmentation may be performed by any suitable process. Examples of suitable fragmentation processes include using nucleases (e.g. restriction endonucleases) and sonication. Preferably, the fragmentation is by sonication.

In Step (e), sequencing adaptors are optionally added to the ends of the nucleic acid fragments. Furthermore, the nucleic acid fragments may be amplified at this time. In this optional step, sequencing adaptors and/or amplification primers (e.g. short double-stranded nucleic acids) are added to both ends of the nucleic acid fragments in order to facilitate the amplification and later sequencing of the nucleic acid fragments.

Each sequencing adaptor may comprise a unique indexing barcode, i.e. a short nucleic acid motif which acts as a unique identifier for that nucleic acid fragment. Preferably, the sequencing adaptors are Next Generation sequencing adap-tors. In some embodiments, the sequencing adaptors com-prise P5 or P7 sequences, which mediate binding to the flow cell and bridge amplification. Internal binding sites for sequencing primers and barcodes may also be added to allow indexing of samples. The sequencing adaptors may be added to the nucleic acid fragments by ligation-mediated PCR.

The nucleic acid fragments may also be amplified (e.g. by PCR) at this time.

For example, 1-20 rounds of PCR may be performed, preferably 3-10 rounds and most preferably about 6 rounds of PCR.

The indexed samples may optionally now be pooled for multiplex sequence analysis.

In Step (f), the nucleic acid fragments are contacted with a targeting nucleic acid which binds to a subgroup of the nucleic acid fragments, wherein the targeting nucleic acid is labelled with the first half of a binding pair. In this step, the desired nucleic acid fragments (e.g. DNA fragments) are prepared for isolation from the background of contaminating nucleic acid fragments.

A targeting nucleic acid is used which has a nucleotide sequence which is complementary or substantially comple-mentary to that of a desired region of the nucleic acids within the nucleic acid sample. The targeting nucleic acid will therefore hybridise, under appropriate conditions, to the desired region of the nucleic acid within the nucleic acid sample.

For example, the desired region of the nucleic acid may be that of a promoter from a particular gene (wherein it is desired to determine which DNA regions interact with that promoter) or it may be that of an enhancer element (wherein it is desired to determine which genes are enhanced by that element).

The targeting nucleic acid may be single- or double-stranded, preferably single-stranded. The targeting nucleic acid may be DNA or RNA, preferably DNA (e.g. a DNA oligonucleotide).

When a restriction endonuclease is used in the production of the 3C library, the targeting nucleic acid preferably contains the ends of the restriction fragment containing the desired region and includes the restriction endonuclease site. In this way, the targeting nucleic acid binds to informative ligation junctions.

Preferably, the concentration of the targeting nucleic acid (e.g. a DNA oligonucleotide) is 5 µM to 1 µM. More preferably, the concentration of the targeting nucleic acid (e.g. a DNA oligonucleotide) is 2.9 µM to 29 pM. Even more preferably, the concentration of the targeting nucleic acid (e.g. a DNA oligonucleotide) is 1 µM to 30 pM, or 300 nM to 30 pM. Even more preferably, the concentration of the targeting nucleic acid (e.g. a DNA oligonucleotide) is 30 nM to 0.3 nM. Most preferably, the concentration of the targeting nucleic acid (e.g. a DNA oligonucleotide) is about 2.9 nM. This applies for each oligonucleotide used.

Preferably, the same targeting nucleic acid is used in any repeat of Step (f).

Targeting nucleic acids (e.g. labelled oligonucleotides) can be designed to bind to any sequence within the genome of the organism being studied. Preferably, the targeting nucleic acid (e.g. a labelled oligonucleotide) is sited (i.e. designed to bind) within a nucleosome-depleted region of a promoter of a gene or non-coding RNA of interest, or a regulatory element (e.g. an enhancer, repressor or CTCF binding site).

Most preferably, the targeting nucleic acid (e.g. a labelled oligonucleotide) is sited (i.e. designed to bind) within the central region of a nucleosome-depleted region of a promoter of a gene or non-coding RNA of interest, or a regulatory element (e.g. an enhancer, repressor or CTCF binding site). As used herein, the term "central" region refers to the middle 50% (preferably middle 30%, 20% or 10%) of the sequence of the nucleosome-depleted region. The term "central" region may also refer to the middle 500, 400, 300, 200, 100 or 50 base pairs of the sequence of the nucleosome-depleted region.

In this way, a very strong and high-resolution picture of the functional interactions controlling gene (or RNA) expression may be obtained. The nucleosome-depleted regions can readily be defined using assays including DNaseI hypersensitivity, ATAC-seq and Chromatin immunoprecipitation.

In some embodiments, the targeting nucleic acid is designed to bind to (or overlap with) a DNaseI hypersensitive site or an ATAC sequence of a promoter of a gene or non-coding RNA of interest, or a regulatory element in the nucleic acid.

In contrast, when the targeting nucleic acid (e.g. a labelled oligonucleotide) is moved 1000 bp to the left or right of the central region, the physical interaction profile is attenuated and it becomes more difficult to define the regulatory contacts precisely (see FIGS. 4a-c).

At loci where gene regulation is already well-defined (such as the alpha and beta globin loci, HBA and HBB), the profiles obtainable from methods of the invention from the central nucleosome-depleted regions at the promoters define all of the known regulatory elements down to almost single base pair resolution (see FIG. 4c). Such resolution has previously been unobtainable.

The transcription factor binding sites at the distal regulatory elements can also be defined from the signal from the central part of a promoter. This can be achieved by using the junction site between the part of the capture read (at the promoter) and the reporter read (at the enhancer). The transcription factor binding sites can be defined because where they bind to the DNA there is a reduction in cut-site density. Thus the strongest signals occur at the unprotected sites in between the transcription factor binding sites. This is similar to DNaseI hypersensitivity foot printing assays.

Examples of binding pairs include biotin with streptavidin. Preferably, the first half of the binding pair is biotin.

In Step (g), the second half of the binding pair is used to isolate the subgroup of nucleic acid fragments which have been bound by the targeting nucleic acid. In this step, the second half of the binding pair is allowed to bind to the first half of the binding pair. In order to aid isolation of the targeted nucleic acid fragments, the second half of the binding pair may be bound to a physical support, for example a column or a bead (e.g. a magnetic bead).

For example, the first half of the binding pair may be biotin and the second half of the binding pair may be a streptavidin-coated bead. The targeted nucleic acid fragments may then be isolated from the background by virtue of the fact that they will be bound to the column or magnetic beads, wherein the background nucleic acids may then be removed.

In some embodiments of the invention, the method is not carried out on a microarray.

In Step (h), the isolated subgroup of nucleic acid fragments is amplified. In this step, the isolated nucleic acid fragments (e.g. DNA fragments) are amplified in order to enrich the desired nucleic acid fragments. Preferably, the amplification is by PCR. Preferably, the amplification comprises 10-40 cycles of PCR amplification, more preferably 12-14 cycles.

In the embodiments of the invention wherein the sequencing adaptors comprise P5 or P7 sequences, PCR primers which bind to the latter sequences may be used.

Steps (d)-(h) of the method of the invention may result in an enrichment of approximately 5-20,000 fold over the corresponding method without Steps (f), (g) and (h).

In Step (j), Steps (f), (g) and (h) may be repeated (in this order). This results in greater enrichment of the desired nucleic acid fragments over the corresponding method without Steps (f), (g) and (h) such that often >90% of the reads contain a sequence targeted by the oligonucleotide capture. Steps (f), (g) and (h) may be repeated (in this order), for example, 1-5 times, e.g. 1, 2, 3, 4 or 5 times.

The steps of the method are preferably carried out in the order specified.

Optionally, the method additionally comprises Step (k), i.e. sequencing the amplified subgroup of nucleic acid fragments. The skilled person will be well aware of numerous DNA sequencing methods which may be used. Preferably, the sequencing is performed using an Illumina platform, e.g. Miseq, HiSeq, NextSeq or NovoSeq, using 150 bp paired end sequences (i.e. 300 bp in total).

The methods of the invention are carried out in vitro or ex vivo.

The disclosure of each reference set forth herein is specifically incorporated herein by reference in its entirety. In particular, the disclosures of WO2017/068379 are specifically incorporated herein by reference.

BRIEF DESCRIPTION OF THE FIGURES

FIG. 4*a* shows a 100 kb section of the alpha globin locus and shows how small changes in the position of the oligonucleotides used for capture change the interaction profile dramatically. In particular, oligonucleotides placed directly over the hypersensitive site at the promoter of the gene reveal highly discrete interactions with the enhancer regulatory elements that control gene expression. Data from NG Capture-C and 4C-seq methods [10, 12, 13] are included to allow comparison with the previously-best available methods.

EXAMPLES

The present invention is further illustrated by the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Figure 1:
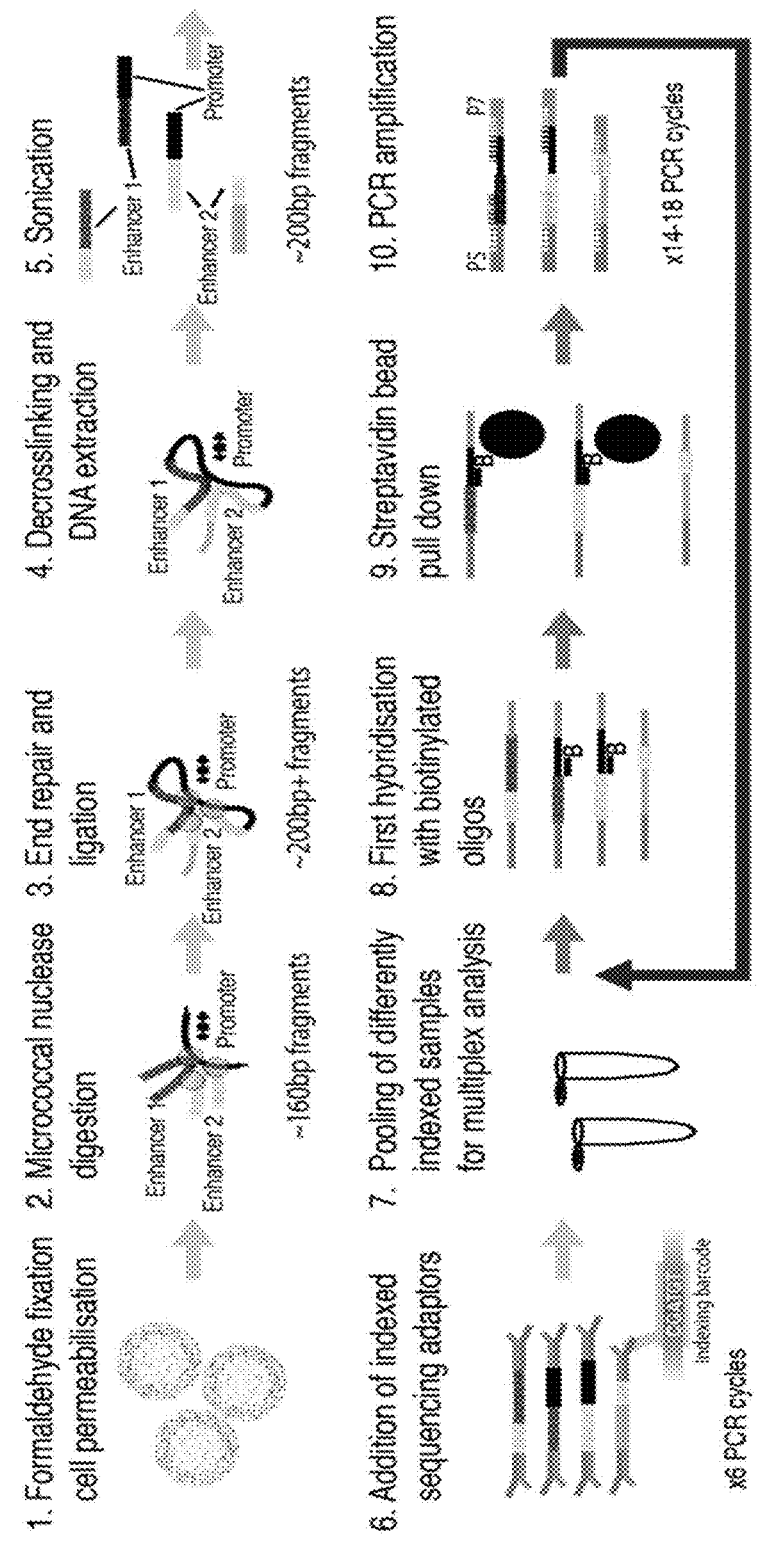
FIG. 1. Overview of the method of the invention for producing a 3C library.
Figure 1:
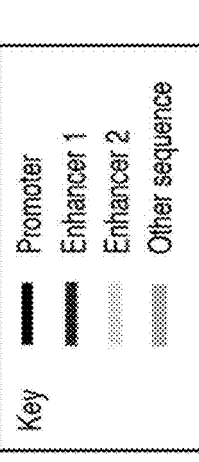
Figure 1:
Figure 2:
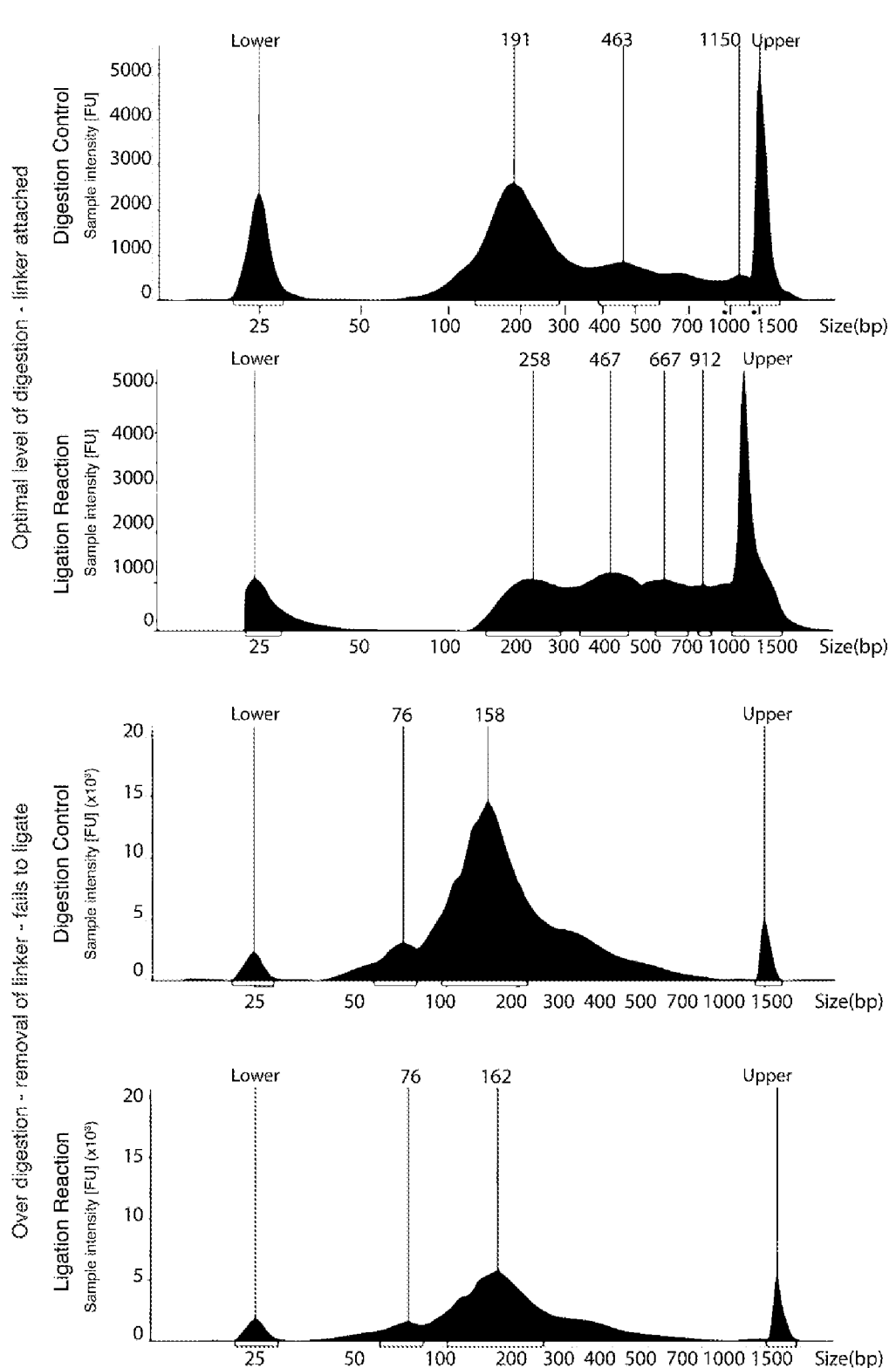
FIG. 2. Nucleosome fragmentation profiles. Following DNA extraction the material was assayed using automated gel electrophoresis (Agilent TapeStation with D1000 reagents). Optimal levels of digestion were obtained when the chromatin was digested predominantly to mono-nucleosomes (180-200 bp) but with the inter-nucleosomal linkers attached (FIGS. 2 and 3). Over-digestion to <160 bp removed the inter-nucleosomal linkers and this meant that it was not possible to ligate fragments in close proximity.
Figure 3:
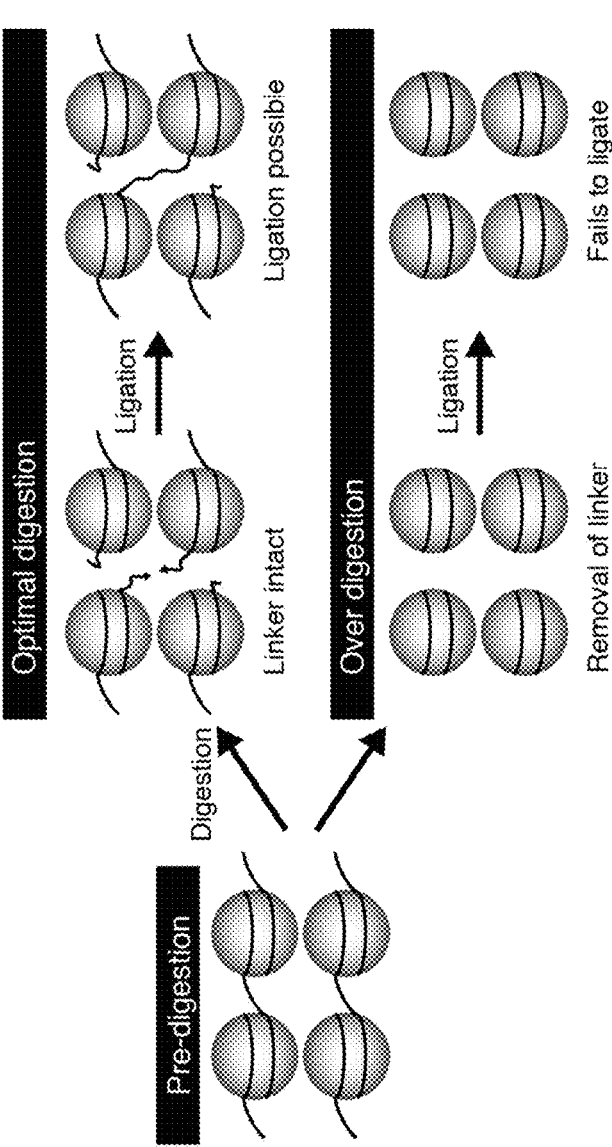
FIG. 3. Model to explain the rationale behind the optimal digestion. Prior to digestion, chromatin is wrapped around nucleosomes. Approximately 148 bp is wrapped around each nucleosome, with a linker sequence of around 20-80 bp. When the sample is digested to a peak fragment size of 180-200 base pairs, the linkers between the nucleosomes are cut, but not digested. This allows the ligation reaction to proceed between different nucleosomes. If the linkers are fully digested between the nucleosomes, then it is impossible to get the ligation reaction to proceed.

Example 1: Preparation of Micrococcal Nuclease
Chromatin Conformation Capture (MCC) Library An overview of the method is shown in FIG. 1.
Fixation
1-2×10$^7$ cells were fixed in 10 ml media with a final concentration of 2% formaldehyde for 10 minutes at room temperature for 10 minutes. This reaction was quenched by adding 1M cold glycine (final concentration 130 mM) and centrifuged for 5 minutes at 300 g/4° C. The supernatant was discarded and the cell pellet was resuspended in phosphate buffered saline, centrifuged (300 g/4° C.) and the supernatant discarded. The cell pellet was then resuspended in phosphate buffered saline and digitonin (Sigma) was added to a final concentration of ~0.05% (sufficient to permeabilise the cells depending on the batch of digitonin). The cells can be snap-frozen and stored at −80° C., if desired, at this point.
Digestion
The permeabilised cells were centrifuged for 5 minutes at 300 g, the supernatant discarded, and the cells were resuspended in a reduced calcium content micrococcal nuclease buffer (Tris HCL pH 7.5 10 mM; CaCl$_2$ 1 mM). A titration of different concentrations of micrococcal nuclease (NEB or Worthington) was used to digest the chromatin (typically ranging from 0.5-40 Kunitz U for a reaction volume of 800 µl containing 2,000,000 cells). This reaction was incubated for 1 hour at 37° C. on an Eppendorf Thermomixer at 800 rpm. Nucleosome digestion profiles are shown in FIG. 2.
The reaction was quenched with EGTA (ethylene glycol-bis(β-aminoethyl ether)-N,N,N',N'-tetraacetic acid (Sigma)) to a final concentration of 5 mM. 200 µl was removed as a control to measure the digestion efficiency. The reaction was centrifuged (5 minutes at 300 g) and the digestion buffer was discarded. The cells were resuspended in phosphate buffered saline and centrifuged again (5 minutes at 300 g) and the supernatant was discarded.
Ligation
End repair and phosphorylation of the DNA was performed prior to ligation. Cells were resuspended in DNA ligase buffer (Thermo Scientific; final concentrations 40 mM Tris HCl pH 7.5, 10 mM MgCl$_2$, 10 mM DTT, 5 mM ATP) supplemented with dNTPs (final concentration 400 uM of each of dATP, dCTP, dGTP and dTTP (Thermo Fischer R0191)) and EGTA 5 mM. T4 Polynucleotide Kinase PNK (NEB M0201L) and DNA Polymerase I (Large (Klenow) Fragment NEB M0210L) were added to final concentrations of 200 U/ml and 100 U/ml respectively and the reaction was incubated at 37° C. for 1 hour. T4 DNA ligase (Thermo Scientific, High Concentration Ligase (30 U/µl) EL0013) was added to a final concentration of 300 U/ml and the reaction was incubated at 16° C. overnight using an Eppendorf Thermomixer at 800 rpm.
De-crosslinking
The chromatin was decrosslinked with proteinase K at 65° C. (>2 hours) and either phenol chloroform with RNAse treatment (Roche: 1119915) or the Qiagen DNeasy blood and tissue kit were used to purify the DNA.
Digestion and ligation efficiencies were assessed using either gel electrophoresis or the Agilent Tapestation (D1000 reagents). This should show >80% mono-nucleosomes and a significant increase in the fragments size in the 3C ligation product (FIG. 2). Over digestion of the chromatin removes the inter-nucleosomal linker sequences and when this occurs, the samples fail to ligate (FIGS. 2 and 3).

Sonication

The oligonucleotide capture protocol was performed as for conventional Next Generation Capture-C. Briefly, the micrococcal nuclease 3C library was sonicated to a mean fragment size of 200 base pairs using a Covaris S220 Focussed Ultrasonicator.

Addition of Sequencing Adaptors

Sequencing adaptors were added using the NEB Ultra II kit and PCR amplified using the Herculase PCR kit (Agilent). These libraries were hybridised typically with 120 base pair biotinylated oligonucleotides (at a concentration of 13 pm-130 fmols/sample depending on the number of oligonucleotides used) for 72 hours using the Roche SeqCap reagents.

Bead Capture

The samples were captured with streptavidin beads (Thermo Fischer M270), washed and amplified using the Roche SeqCap reagents and standard protocols. A second round of oligonucleotide capture was performed with the same oligonucleotides and reagents with only a 24-hour hybridization reaction.

Sequencing

The material was sequenced using the Illumina platform with 300 base pair reads (150 base pair paired end).

Results

The data was analysed as illustrated in FIG. 4. FIG. 4 shows data from the Micrococcal nuclease Capture-C (MCC) experiment. In this experiment, data was generated for 35 genes simultaneously. The experimental design included a central capture oligonucleotide designed to capture contacts directly from the middle of the hypersensitive site at the promoter of the gene and two flanking oligos, one ~1 kb upstream (labelled cleft') and one ~1 kb downstream (labelled 'right'). The data show that the resolution of MCC is much greater than that achievable by the best methods previously available (NG Capture-C and 4C-seq) for defining interaction profiles at high resolution in mammalian genomes. In addition, the data have a substantially improved resolution compared to the all v all contact maps in yeast generated using the Micro-C protocol [14] despite the much greater genome size.

Figure 4A:
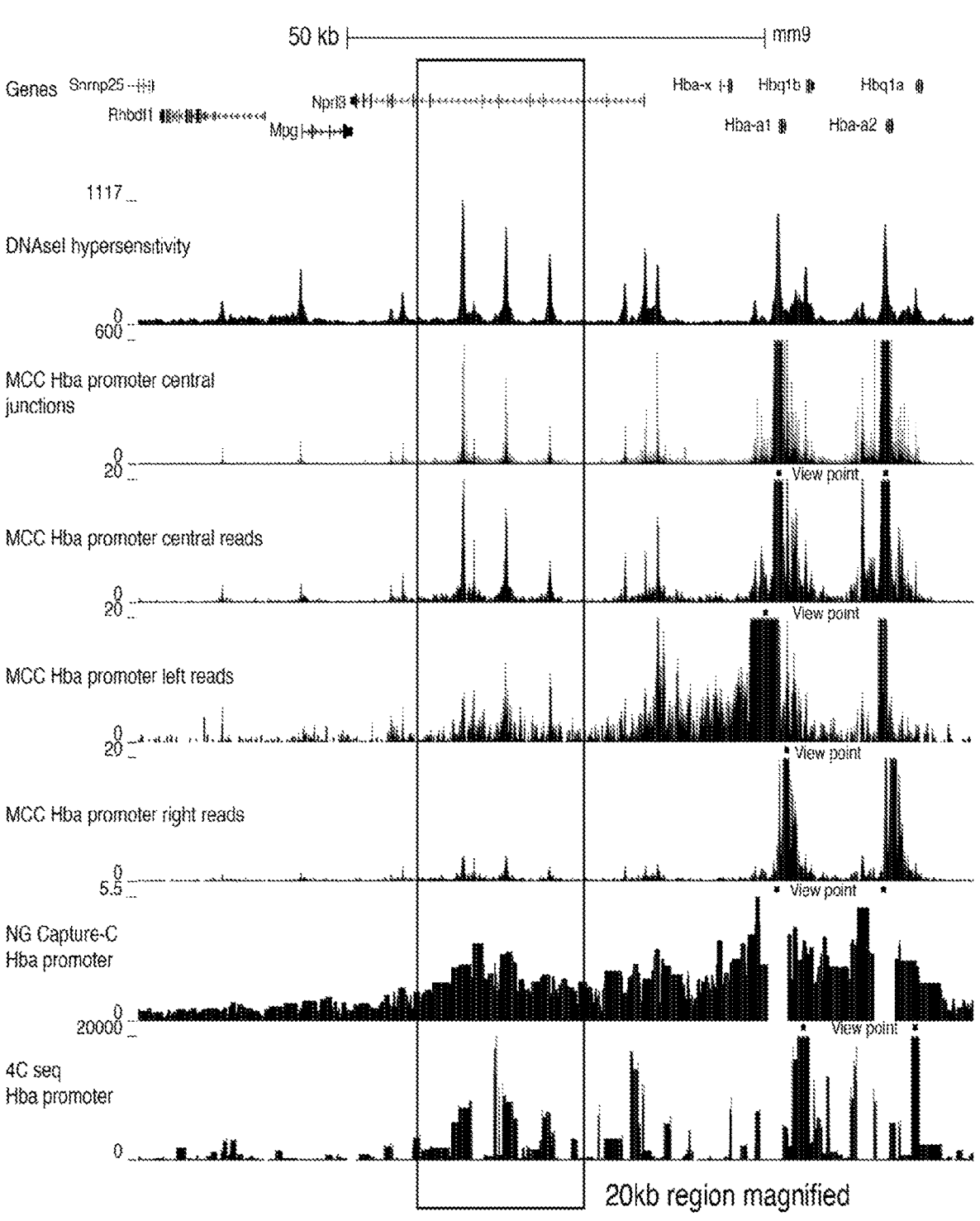
FIG. 4*a, b and c*. Comparison of data generated by different 3C methods. These panels show the increased resolution obtained using the method of the invention in comparison to data from Hsieh et al. [15].
Figure 4B:
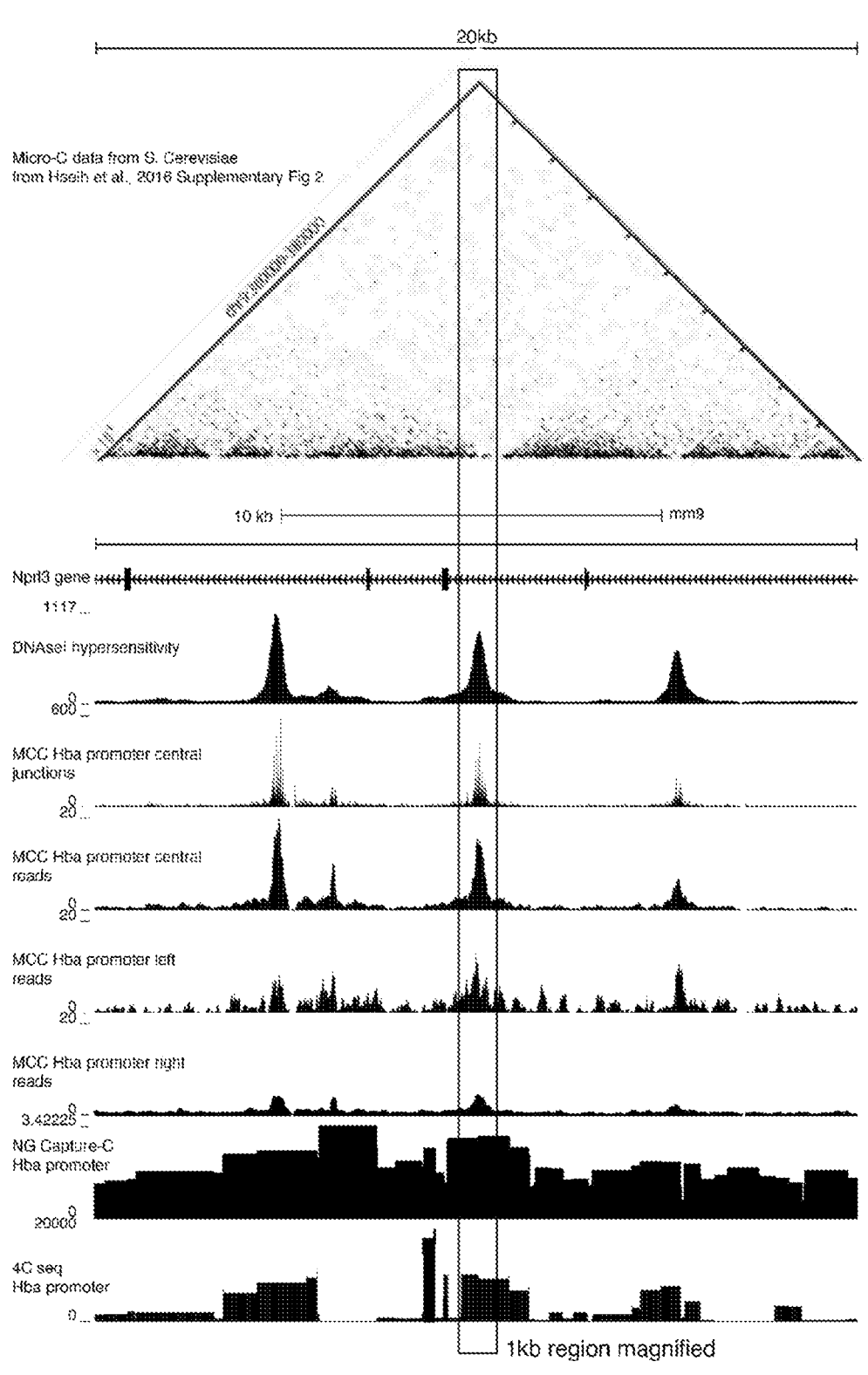
FIG. 4*b* shows a 20 kb section from FIG. 4*a* and includes 20 kb data from Hsieh et al. [15], generated from *S. cerevisiae* to allow comparison.

The position of the oligonucleotides used for capture change the interaction profile dramatically. When oligonucleotides are placed directly over the hypersensitive site at the promoter of the gene, MCC reveals highly discrete interactions with the enhancer regulatory elements that are known to control gene expression (FIGS. 4a, b, c). However, when the biotinylated oligonucleotides are placed ~1 kb upstream or downstream from the central oligo position on the DNase site, the profile changes and the interactions are more diffuse. Data from NG Capture-C and 4C-seq are included to allow comparison with the previously-best available methods for defining one vs all interaction profiles in large mammalian genomes. FIG. 4b shows a 20 kb section from FIG. 4a and includes 20 kb data from Hsieh et al. [15] generated from S. cerevisiae.

Figure 4C:
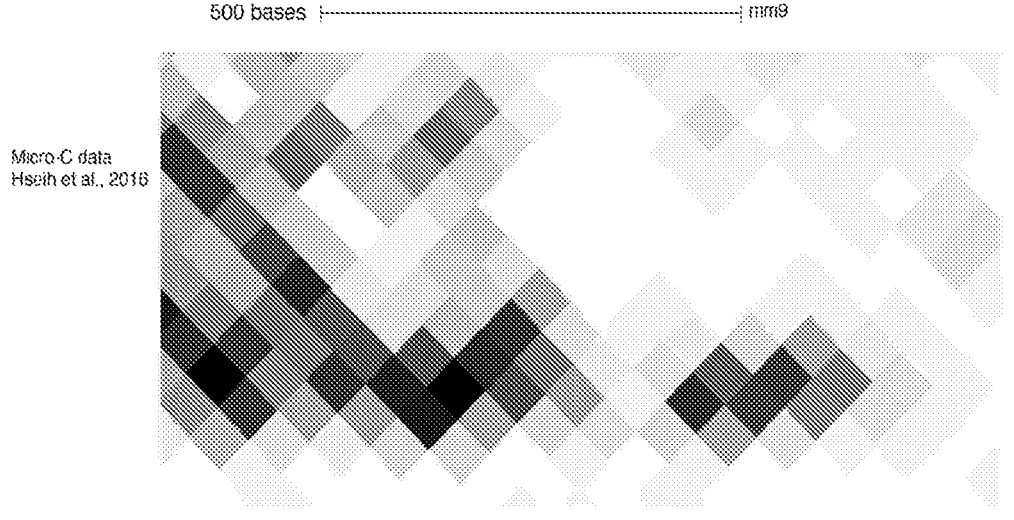
FIG. 4*c* shows a 1 kb section from FIG. 4*b*, which highlights the resolution obtainable from the method of the invention. When the ligation junctions are plotted, this gives close to single base pair resolution and this potentially highlights the binding sites of transcription factors within the enhancer region.
Figure 4C:
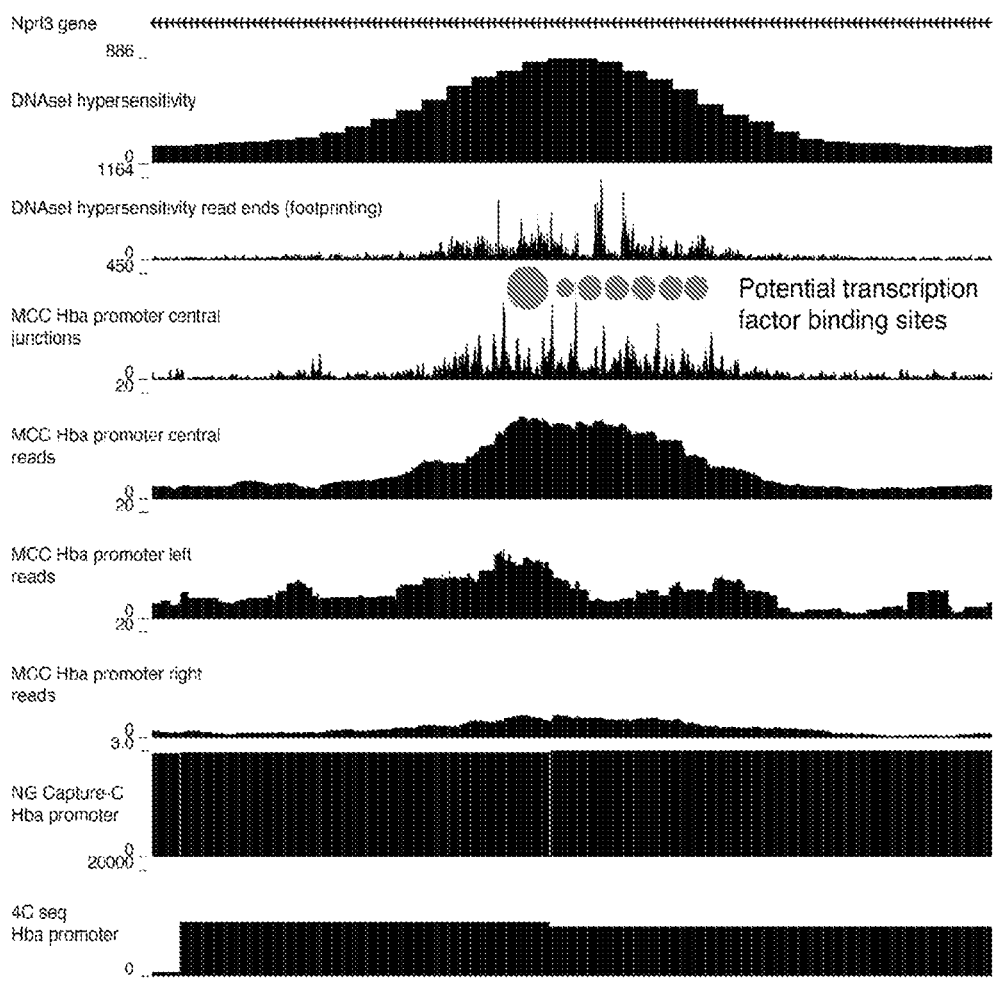

FIG. 4c shows a 1 kb section from FIG. 4b; this highlights the resolution obtainable from the method of the invention. When the ligation junctions are plotted (in contrast to a pile up of the whole reads shown in the other tracks), this gives close to single-base pair resolution. This highlights the potential transcription factor binding sites within the enhancer region in a similar to DNase I hypersensitivity footprinting data. In this experiment another 35 genes were analysed and these data show similar improvements in resolution.

Example 2: Effect of Digitonin on Resolution

Figure 5:
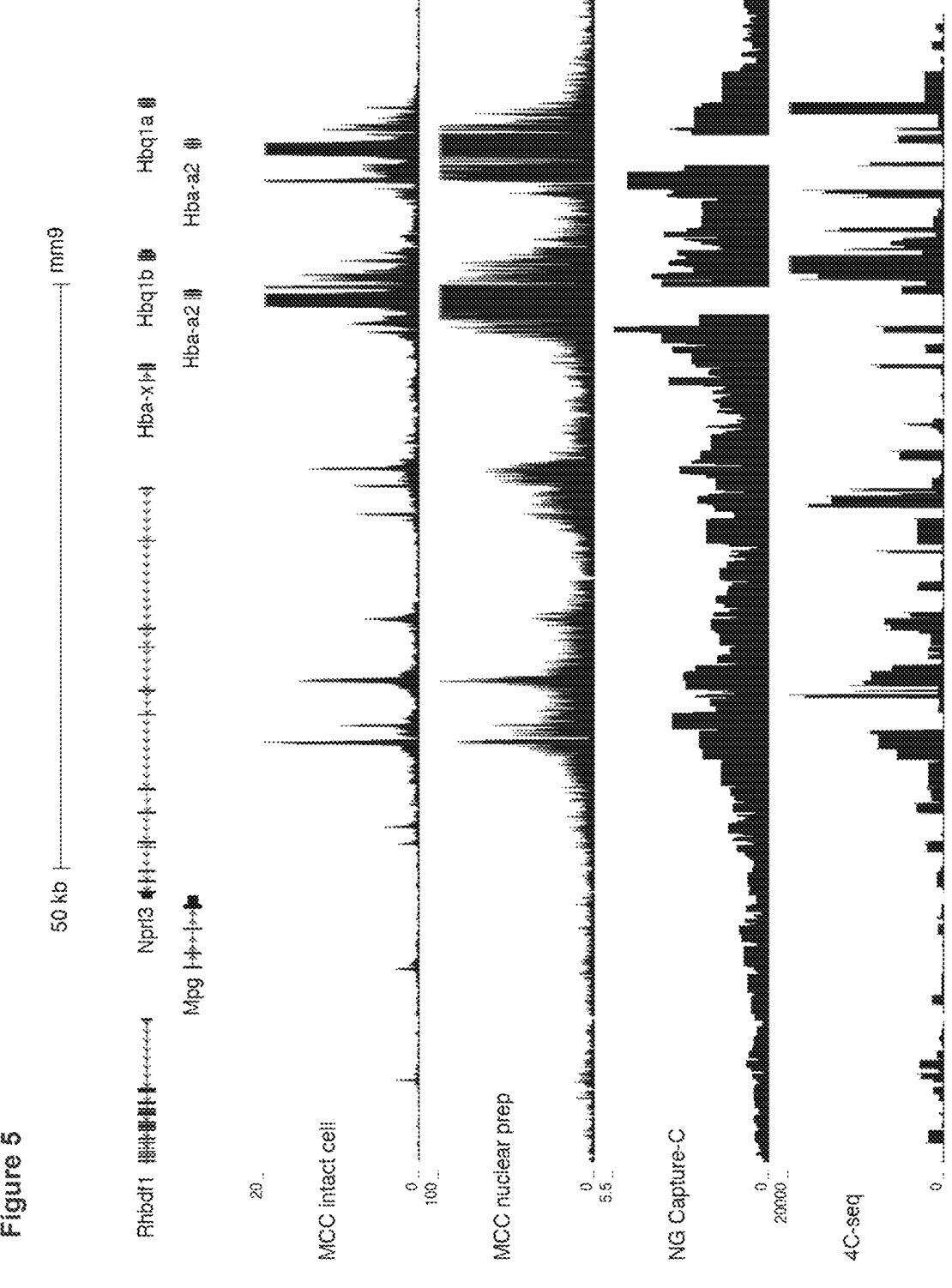
FIG. 5 shows a comparison of MCC performed with an intact whole cell preparation compared to a nuclear preparation.

FIG. 5 shows a comparison of MCC performed with an intact whole-cell preparation compared to a nuclear preparation. The whole-cell preparation shows much more distinct peaks with the enhancer elements in comparison to the data generated from nuclei. NG Capture-C and 4C-seq data were included for comparison (both of these were generated from 3C libraries generated from nuclei rather than from intact cells).

Comparative Example 3: Resolution Obtained Using Micro-C Method

Figure 6:
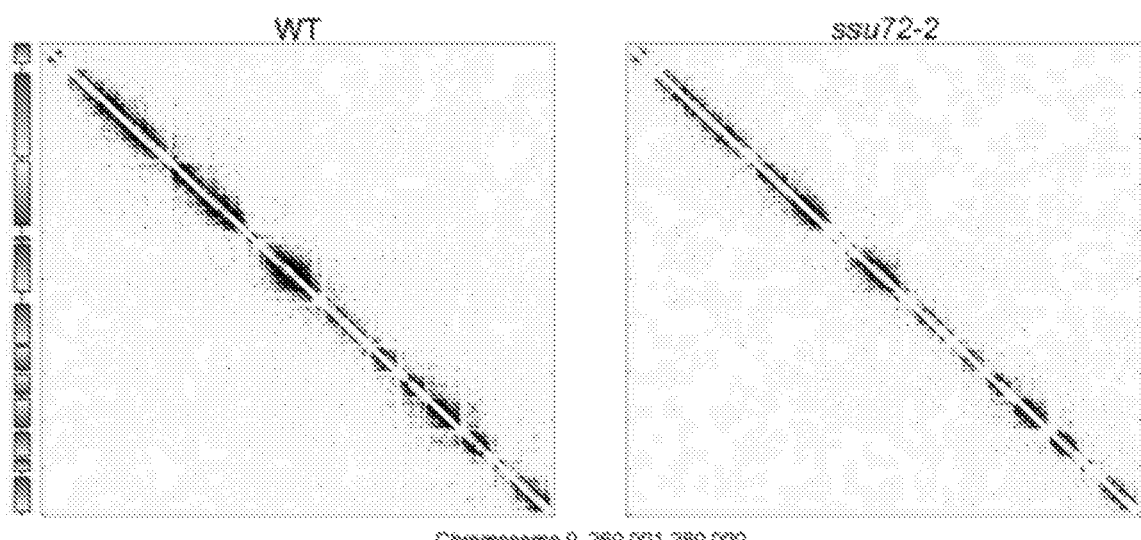
FIG. 6. Micro-C data. This illustrates the nucleotide sequence resolution obtained using a method of the prior art (taken from FIG. 5 of Hsieh et al. [14]).
Figure 6:
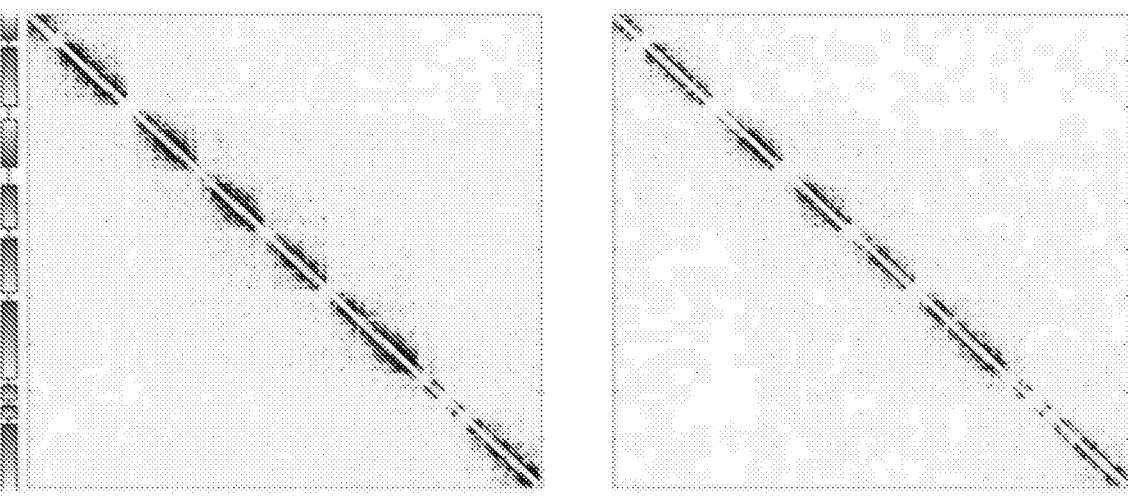

For comparative purposes only, reference is made to the Micro-C method of the prior art (Hsieh et al., 2015 & 2016 [14, 15]). FIG. 4 shows data from Hsieh et al. [15] (Supplementary FIG. 2) showing a 20 kb region of yeast chromosome IX and FIG. 6 herein (reproduced from FIG. 5C of Hsieh et al. [14]) shows two 20 kb×20 kb matrices showing wild-type and ssu72-2 Micro-C data. These illustrate the lower level of resolution obtained in that Micro-C method.

REFERENCES

1. Wang, Z., Gerstein, M. & Snyder, M. RNA-Seq: a revolutionary tool for transcriptomics. Nat Rev Genet 10, 57-63 (2009).
2. Mikkelsen, T. S. et al. Genome-wide maps of chromatin state in pluripotent and lineage-committed cells. Nature 448, 553-60 (2007).
3. Robertson, G. et al. Genome-wide profiles of STAT1 DNA association using chromatin immunoprecipitation and massively parallel sequencing. Nat Methods 4, 651-7 (2007).
4. Hesselberth, J. R. et al. Global mapping of protein-DNA interactions in vivo by digital genomic footprinting. Nat Methods 6, 283-9 (2009).
5. Buenrostro, J. D., Giresi, P. G., Zaba, L. C., Chang, H. Y. & Greenleaf, W. J. Transposition of native chromatin for fast and sensitive epigenomic profiling of open chromatin, DNA-binding proteins and nucleosome position. Nat Methods 10, 1213-8 (2013).
6. Dekker, J., Rippe, K., Dekker, M. & Kleckner, N. Capturing chromosome conformation. Science 295, 1306-11 (2002).
7. Tolhuis, B., Palstra, R. J., Splinter, E., Grosveld, F. & de Laat, W. Looping and interaction between hypersensitive sites in the active beta-globin locus. Mol Cell 10, 1453-65 (2002).
8. Noordermeer, D. et al. The dynamic architecture of Hox gene clusters. Science 334, 222-5 (2011).
9. Sanyal, A., Lajoie, B. R., Jain, G. & Dekker, J. The long-range interaction landscape of gene promoters. Nature 489, 109-13 (2012).
10. van de Werken, H. J. et al. Robust 4C-seq data analysis to screen for regulatory DNA interactions. Nat Methods 9, 969-72 (2012).
11. de Laat, W. & Duboule, D. Topology of mammalian developmental enhancers and their regulatory landscapes. Nature 502, 499-506 (2013).

12. Davies J. O. J., Oudelaar A. M., Higgs D. R. and Hughes J. R. How best to identify chromosomal interactions: a comparison of approaches. Nature Methods 2017, 14 (2), 125-134

13. Davies J. O. J., Telenius J. M., McGowan S., Roberts N. A., Taylor S., Higgs D. R. and Hughes J. R. 'Multiplexed analysis of chromosome conformation at vastly improved sensitivity', Nature Methods 2016; 13, 74-80

14. Hsieh T. H., Weiner A., Lajoie B., Dekker J., Friedman N., Rando O. J. Mapping Nucleosome Resolution Chromosome Folding in Yeast by Micro-C. Cell. 2015 Jul. 2; 162(1):108-19.

15. Hsieh T. S. Fudenberg G., Goloborodko A., Rando O. J. Micro-C XL: assaying chromosome conformation from the nucleosome to the entire genome. Nat Methods. 2016 December; 13(12):1009-1011.

The invention claimed is:

1. A method comprising producing nucleic acids with unlabeled ends, comprising:
   (a) treating chromatin in a population of eukaryotic cells by:
      (i) immobilising the chromatin within the cells in the population of eukaryotic cells;
      (ii) permeabilising or removing cell membranes of the eukaryotic cells; and
      (iii) fragmenting the immobilised chromatin within the cells to produce nucleic acids with unlabeled ends comprising >70% mono-nucleosomes of 180-200 bp;
   (b) ligating the nucleic acids with unlabeled ends comprising the mono-nucleosomes of 180-200 bp to produce ligated nucleic acid fragments; and
   (c) de-immobilising the ligated nucleic acid fragments.

2. The method of claim 1, wherein in Step (i), the chromatin is immobilised by cross-linking the chromatin.

3. The method of claim 1, wherein:
   (a) the outer cell membranes and nuclear membranes are permeabilised;
   (b) the outer cell membranes and/or nuclear membranes are not lysed;
   (c) the outer cell membranes or nuclear membranes are not completely removed;
   (d) the outer cell membranes and nuclear membranes of the cells are permeabilised without removing the outer cell membranes or nuclear membranes;
   (e) the cell membranes are removed and the nuclear membranes are permeabilised but not removed;
   (f) the cell membranes are removed and the nuclear membranes are removed; or
   (g) the process comprises (ii) permeabilising the cell membranes of the eukaryotic cells; and (iii) fragmenting the immobilised chromatin within the cells to produce nucleic acid fragments.

4. The method of claim 1, wherein in Step (iii), the immobilised chromatin is fragmented using an endo-exonuclease or using micrococcal nuclease.

5. The method of claim 1, wherein in Step (iii), the immobilised chromatin is fragmented such that mono-nucleosomes are produced, wherein the inter-nucleosomal linkers are not digested to completion.

6. The method of claim 1, wherein the eukaryotic cells are mammalian cells and wherein the number of cells in the population of mammalian cells is 1-10,000, 10,000-1 million, or 1 million to 100 million.

7. A kit for identifying nucleic acid regions within a nucleic acid sample which interact with one another, the kit comprising buffers and reagents for performing a method as defined in claim 1.

8. The method of claim 1, wherein the eukaryotic cells are mammalian cells.

9. The method of claim 1, wherein the fragmenting in step (iii) is carried out using micrococcal nuclease.

10. The method of claim 1, wherein the fragmenting is performed without use of a restriction endonuclease.

11. The method of claim 1, wherein the fragments comprise mono-nucleosomes and linkers that are not digested to completion.

12. The method of claim 6, wherein the mammal is a human.

* * * * *